United States Patent
Gao et al.

(10) Patent No.: US 6,231,887 B1
(45) Date of Patent: *May 15, 2001

(54) PHARMACEUTICAL COMPOSITION FOR ACIDIC LIPOPHILIC COMPOUNDS IN A FORM OF A SELF-EMULSIFYING FORMULATION

(75) Inventors: Ping Gao, Portage; Walter Morozowich, Kalamazoo, both of MI (US)

(73) Assignee: Pharmacia & Upjohn Company, Kalamazoo, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/122,927

(22) Filed: Jul. 27, 1998

Related U.S. Application Data

(60) Provisional application No. 60/054,012, filed on Jul. 29, 1997.

(51) Int. Cl.⁷ .............................. A61K 9/48; A61K 31/44; A61K 31/35
(52) U.S. Cl. ..................... 424/451; 424/455; 424/456; 516/336; 516/456; 516/937
(58) Field of Search .................................. 424/451, 455, 424/456; 514/336, 456, 937

(56) References Cited

U.S. PATENT DOCUMENTS

| | | |
|---|---|---|
| 4,230,702 | 10/1980 | Eckert et al. . |
| 5,071,643 | 12/1991 | Yu et al. . |
| 5,360,615 | 11/1994 | Yu et al. . |
| 5,376,688 | 12/1994 | Morton et al. . |
| 5,504,068 * | 4/1996 | Komiya .................................. 514/11 |

FOREIGN PATENT DOCUMENTS

| | | |
|---|---|---|
| 2 222 770 | 3/1990 | (GB) . |
| 2 228 198 | 8/1990 | (GB) . |
| 2 257 359 | 10/1996 | (GB) . |
| WO95/30670 | 11/1995 | (WO) . |
| WO96/39142 | 12/1996 | (WO) . |
| WO98/22106 | 5/1998 | (WO) . |

* cited by examiner

Primary Examiner—Gollamudi S. Kishore
(74) Attorney, Agent, or Firm—Lucy X. Yang

(57) ABSTRACT

The present invention provides a novel pharmaceutical composition based on the use of a particular amount of basic amine which comprises a pyranone compound as a pharmaceutically active agent, a basic amine in an amount of from about 0.1% to about 10% by weight of the total composition, one or more pharmaceutically acceptable solvents, and one or more pharmaceutically acceptable surfactants. In addition, the composition may further comprises one or more pharmaceutically acceptable oils. The composition is in a form of self-emulsifying formulation which provides high concentration and high oral bioavailability for lipophilic pyranone compounds.

29 Claims, No Drawings

PHARMACEUTICAL COMPOSITION FOR ACIDIC LIPOPHILIC COMPOUNDS IN A FORM OF A SELF-EMULSIFYING FORMULATION

CROSS-REFERENCE TO RELATED APPLICATION

This application claims the benefit of the following provisional application: U.S. Ser. No. 60/054,012, filed Jul. 29, 1997, under 35 USC 119(e)(i).

FIELD OF THE INVENTION

The present invention relates to novel pharmaceutical compositions in a form of a self-emulsifying formulation containing a basic amine which provide high concentration and high oral bioavailability for pyranone compounds which are inhibitors of retroviral protease.

BACKGROUND OF THE INVENTION

It has recently been discovered that certain pyranone compounds inhibit retroviral protease and thus they are useful for treating patients infected with human immunodeficiency virus (HIV) which results in acquired immunodeficiency syndrome (AIDS). In particular, the pyranone compound of formula I has been found to be especially effective as an inhibitor of retroviral protease.

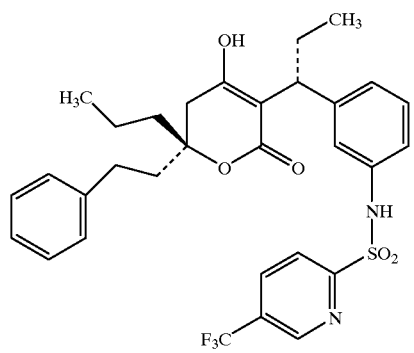

However, like many other HIV protease inhibitors, these compounds are characteristically lipophilic and thus poorly water soluble. For example, the compound of formula I has an aqueous solubility about 1 $\mu$g/ml in the buffer of pH 6.5 (close to the pH of the intestine), which is considered to have extremely poor aqueous solubility and would be expected to provide very low oral bioavailability in the free acid form. It is well known that an active drug substance or therapeutic moiety administered by any route must possess some aqueous solubility for systemic absorption and therapeutic response. Poorly water soluble compounds often exhibit either incomplete or erratic absorption and thus produce a minimal response at desired dosage.

Attempts were made to identify salts of the pyranone compounds in solid forms which could improve aqueous solubility. An overriding defect which has however remained is that the formulation in the form of salt are prone to precipitation of the parent free acid in the gastrointestinal tract and hence are not capable to provide a dosage in the desired high concentration to permit convenient use and yet meet the required criteria in terms of bioavailability.

Recognizing the problems, the present invention is directed toward pharmaceutical compositions in a form of self-emulsifying formulations which provide high concentration and high oral bioavailability for pyranone compounds. In particular it has been discovered that the compositions of the present invention allow the preparation of self-emulsifying formulations containing a pyranone inhibitor of retroviral protease in an exceedingly high concentration up to about 500 mg/g to permit convenient oral administration while at the same time achieving improved bioavailability, which is at least three fold higher than the aqueous suspension of the free acid.

INFORMATION DISCLOSURE

The International Publication No. WO 95/30670 discloses pyranone compounds useful to treat retroviral infections.

The International Publication No. WO 96/39142 discloses compositions which increase the bioavailability of protease inhibitors.

UK Patent Application, GB 2,222,770A discloses pharmaceutical compositions comprising a cyclosporin in microemulsion pre-concentrate and microemulsion form.

UK Patent Application, GB 2,228,198A discloses pharmaceutical compositions comprising a cyclosporin as active ingredient, a fatty acid triglyceride, a glycerol fatty acid partial ester or propylene glycol or sorbitol complete or partial ester and a tenside having an HLB of at least 10.

UK Patent, GB 2,257,359B discloses pharmaceutical compositions suitable for oral administration comprising a cyclosporin, 1,2-propylene glycol, a mixed mono-, di-, and tri-glyceride and a hydrophilic surfactant.

U.S. Pat. No. 4,230,702 discloses a readily enterally absorbable pharmaceutical composition of pharmacologically active agents, which per se are poorly enterally absorbable.

U.S. Pat. Nos. 5,071,643, 5,360,615 and 5,376,688 disclose highly concentrated solutions of an acidic pharmaceutical agent suitable for filling soft gels comprising the acidic pharmaceutical agent and a solvent system, the solvent system comprising polyethylene glycol, water and an ionic species.

SUMMARY OF THE INVENTION

One object of the present invention is to provide a pharmaceutical composition comprising a pyranone compound of formulas I, II, III or IV which provides high oral bioavailability.

A further object of the present invention is to provide a pharmaceutical composition containing a high drug load of a pyranone compound of formulas I, II, III or IV for convenient administration.

Another object of the present invention is to provide pharmaceutical compositions which exhibit adequate physical and chemical stability in a self-emulsifying formulation.

Still another object of the present invention is to provide a liquid composition for soft elastic capsules.

The objects of the present invention have been accomplished in that the present invention provides pharmaceutical compositions in a form of a self-emulsifying formulation which allow a high loading of pyranone compounds (up to about 500 mg/g) while at the same time achieving good oral bioavailability.

The present invention specifically provides a pharmaceutical composition based on the use of a particular amount of a basic amine which comprises:

(a) a pyranone compound of formula I, II, III or IV, (b) an amine in an amount of from about 0.1% to about 10% by weight of the total composition, (c) one or more pharmaceutically acceptable solvents, and (d) one or more pharmaceutically acceptable surfactants.

In addition, the composition may further comprise one or more pharmaceutically acceptable oils.

DETAILED DESCRIPTION OF THE INVENTION

In accordance with the present invention, there are pharmaceutical compositions comprising a pyranone compound as a pharmaceutically active agent in a self-emulsifying formulation vehicle.

For the purpose of the present invention, the term "pyranone compounds" refers to compounds of formula II

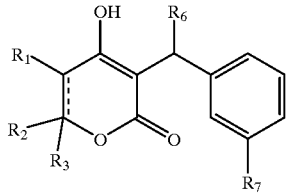

wherein $R_1$ is H—; $R_2$ is $C_3$-$C_5$ alkyl, phenyl-$(CH_2)_2$—, het-$SO_2NH$—$(CH_2)_2$—, cyclopropyl-$(CH_2)_2$—, F-phenyl-$(CH_2)_2$—, het-$SO_2NH$-phenyl-, or $F_3C$—$(CH_2)_2$—; or $R_1$ and $R_2$ taken together are a double bond; $R_3$ is $R_4$—$(CH_2)_n$—$CH(R_5)$—, $H_3C$—$[O(CH_2)_2]_2$—$CH_2$—, $C_3$-$C_5$ alkyl, phenyl-$(CH_2)_2$—, het-$SO_2NH$—$(CH_2)_2$—, $(HOCH_2)_3C$—$NH$—$C(O)$—$NH$—$(CH_2)_3$—, $(H_2C)(H_2N)$ $CH$—$(CH_2)_2$—$C(O)$—$NH$—$(CH_2)_3$—, piperazin-1-yl-C (O)—N H —$(CH_2)_3$, $HO_3S(CH_2)_2$—$N(CH_3)$—$C(O)$—$(CH_2)_6$—$C(O)$ —$NH$—$(CH_2)_3$—, cyclopropyl-$(CH_2)_2$—, F-phenyl-$(CH_2)_2$ —, het-$SO_2NH$-phenyl, or $F_3C$—$(CH_2)_2$—; n is 0, 1 or 2; $R_4$ is phenyl, het, cyclopropyl, $H_3C$—$[O(CH_2)_2]_2$—, het-$SO_2NH$—, Br—, $N_3$—, or $HO_3S(CH_2)_2$—$N(CH_3)$—$C$ (O)—$(CH_2)_6$—$C(O)$—$NH$—; $R_5$ is —$CH_2$—$CH_3$, or —$CH_2$-cyclopropyl; $R_6$ is cyclopropyl, $CH_3$—$CH_2$—, or t-butyl; $R_7$ is —$NR_8SO_2$-het, —$NR_8SO_2$-phenyl, optionally substituted with $R_9$, —$CH_2$—$SO_2$-phenyl, optionally substituted with $R_9$, or —$CH_2$—$SO_2$-het; $R_8$ is —H, or —$CH_3$; $R_9$ is —CN, —F, —OH, or —$NO_2$; wherein het is a 5-, 6- or 7-membered saturated or unsaturated ring containing from one to three heteroatoms selected from the group consisting of nitrogen, oxygen and sulfur; and including any bicyclic group in which any of the above heterocyclic rings is fused to a benzene ring or another heterocycle, optionally substituted with —$CH_3$, —CN, —OH, —$C(O)OC_2H_5$, —$CF_3$, —$NH_2$, or —$C(O)$—$NH_2$; or a pharmaceutically acceptable salt thereof. The preferred compound of formula II is a compound of formula I.

The term "pyranone compounds" also refers to compounds of formula III and formula IV

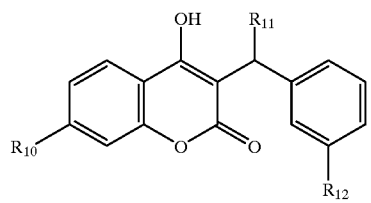

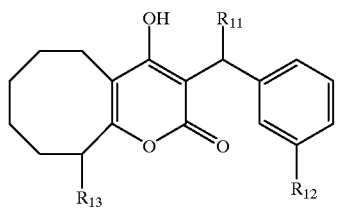

wherein $R_{10}$ is H—, $CH_3O$—, or $CH_3O$—$[(CH_2)_2O]_3$—; $R_{11}$ is cyclopropyl, or —$CH_2$—$CH(CH_3)_2$; $R_{12}$ is —$NR_{14}SO_2$-phenyl, optionally substituted with $R_{15}$, —$NR_{14}SO_2$-het, —$CH_2$—$SO_2$-phenyl, optionally substituted with $R_{15}$, or —$CH_2$—$SO_2$-het; $R_{13}$ is —H, —$(CH_2)_2$—$CH_3$, —$CH_2$-cyclopropyl, or —$CH_2$-phenyl; $R_{14}$ is —H, or —$CH_3$; $R_{15}$ is —CN, —F, —$CH_3$, —COOH, or —OH; het is a 5-, 6- or 7-membered saturated or unsaturated ring containing from one to three heteroatoms selected from the group consisting of nitrogen, oxygen and sulfur; and including any bicyclic group in which any of the above heterocyclic rings is fused to a benzene ring or another heterocycle; optionally substituted with one or two —$CH_3$, —CN, —$C(O)OC_2H_5$, or —OH; or a pharmaceutically acceptable salt thereof.

These compounds inhibit retroviral protease and thus inhibit the replication of the virus. They are useful for treating patients infected with human retrovirus such as human immunodeficiency virus (strains of HIV-1 or HIV-2) or human T-cell leukemia viruses (HTLV-I or HTLV-II) which results in acquired immunodeficiency syndrome (AIDS) and/or related diseases. The compounds of formulas I, II, III and IV are disclosed and claimed in International Application No. PCT/US95/05219, incorporated herein by reference, and may be prepared according to the procedures described in International Publication No. WO 95/30670. In particular, the pyranone compound of formula I has been found to be especially effective as an inhibitor of retroviral protease.

The term "self-emulsifying formulation" used herein refers to a concentrated composition capable of generating emulsions or microemulsions upon mixing with sufficient aqueous media.

The emulsions or microemulsions generated from the present invention are conventional solutions comprising a hydrophilic phase and a lipophilic phase. Microemulsions are also characterized by their thermodynamic stability, optical transparency and small average droplet size, generally less than about 0.15 micron.

The term "self-emulsifying formulation vehicle" refers to a composition comprising an amine in an amount of from about 0.1% to about 10% by weight of the total composition, one or more pharmaceutically acceptable solvents, and one or more pharmaceutically acceptable surfactants. Optionally, the self-emulsifying formulation vehicle may further comprise one or more pharmaceutically acceptable oils.

The amount of active ingredient in the composition may vary or be adjusted widely depending on the intended route of administration, the potency of the particular active ingredient being used, the severity of the retroviral infection and the required concentration. If desired, however, a pyranone compound as an inhibitor of retroviral protease can be present in the self-emulsifying vehicle of the present invention in an amount up to about 500 mg/g with excellent dispersiability and high oral bioavailability in vivo typically reaching 60–96% in rats.

The compositions of the present invention with high oral bioavailability (80–96% in rats) demonstrate an almost transparent or translucent solution upon dilution with water, which indicates that a microemulsion is formed.

The compositions of the present invention with moderately high bioavailability (60–70% in rats) usually show a visible fine white emulsion without precipitation of the drug upon dilution with water, which indicates that an emulsion is formed.

In one aspect, the present invention specifically provides a pharmaceutical composition based on the use of particular oil phase which comprises:

(a) a pyranone compound of formulas I, II, III or IV as a pharmaceutically active agent, (b) an amine in an amount of from about 0.1% to about 10% by weight of the total composition, (c) one or more pharmaceutically acceptable solvents, and (d) one or more pharmaceutically acceptable surfactants.

In addition, the composition may further comprise one or more pharmaceutically acceptable oils.

The term "pharmaceutically acceptable" used herein refers to those properties which are biologically compatible with the treated subjects from a pharmacological and toxicological point of view.

Solvents of the present invention refer to propylene glycol, polypropylene glycol, polyethylene glycol (such as PEG300, 400, 600, etc.), glycerol, ethanol, triacetin, dimethyl isosorbide, glycofirol, propylene carbonate, water, dimethyl acetamide or a mixture thereof.

The preferred solvent is propylene glycol or a mixture comprising propylene glycol and 95% (v/v) ethanol (hereinafter ethanol). In the mixture of propylene glycol and ethanol, propylene glycol is in an amount of from about 50% to about 95%.

Surfactants of the present invention refer to non-ionic surfactants including Polyoxyl 40 hydrogenated castor oil sold under the trade name, among the others, Cremophor RH40; Polyoxyl 35 castor oil sold under the trade name, among the others, Cremophor EL or Cremophor EL; Polysorbates; Solutol HS-15; Tagat TO; Peglicol 6-oleate; Polyoxyethylene stearates; Saturated Polyglycolyzed Glycerides; or Poloxamers; all of which are commercially available. The preferred surfactant is Cremophor RH140, Cremophor EL or Polysorbate 80.

Saturated Polyglycolyzed Glycerides used herein include Gelucire 44/14 or Gelucire 50/13.

Polyoxyethylene stearates used herein include Poloxyl 6 stearate, Poloxyl 8 stearate, Poloxyl 12 stearate and Poloxyl 20 stearate.

Poloxamers used herein include Poloxamer 124, Poloxamer 188, Poloxamer 237, Poloxamer 338 and Poloxamer 407.

Polysorbates used herein include Polysorbate 20, Polysorbate 40, Polysorbate 60 and Polysorbate 80.

The term "amine" used herein refers to lower alkylamine such as, for example, ethanolamine, diethanolamine, triethanolamine, dimethylaminoethanol, tris(hydroxymethyl)aminomethane or ethylenediamine; quaternary ammoniums such as, for example, choline hydroxide; basic amino acids such as, for example, arginine lysine or guanidine. The preferred basic amine is lower alkylamine or quaternary ammonium. The preferred lower alkylamine is dimethylaminoethanol or tris(hydroxymethyl)aminomethane.

Oil useful in forming the composition of the present invention includes a broad spectrum of water-immiscible materials such as soybean oil, avocado oil, squalene oil, sesame oil, olive oil, canola oil, corn oil, rapeseed oil, safflower oil, sunflower oil, fish oils, flavored oils, water insoluble vitamins and mixtures thereof. The preferred oils are the medium chain fatty acid glyceride such as commercially available under the trade names, among the others, Maisine, Miglyol 812, Captex 355, Myritol, Capmul MCM, Captex 200, Myvacet, Myverol 18–92, Arlacel 186, Neobee, Mazol or commercially available monoolein, diolein and triolein. The more preferred oils of the present invention is Capmul MCM, monoolein, diolein, triolein, monolinoleate, dilinoleate, trilinoleate or Maisine.

A typical composition according to the present invention comprises:

(a) a pyranone compound of formulas I, II, III or IV in an amount of from about 1% to about 50% by weight of the total composition, (b) an amine in an amount of from about 0.1% to about 10% by weight of the total composition, (c) one or more pharmaceutically acceptable solvents in an amount of from about 10% to about 30% by weight of the total composition, and (d) a pharmaceutically acceptable surfactant in an amount of from about 10% to about 50% by weight of the total composition.

Optionally, the composition further comprises one or more oils in an amount of from about 5% to 35% by weight of the total composition.

A preferred composition of the present invention comprises:

(a) a pyranone compound of formulas I, II, HI or IV in an amount of from about 20% to about 30% by weight of the total composition, (b) a dimethylaminoethanol or tris(hydroxymethyl) aminomethane in an amount of from about 0.1% to about 7% by weight of the total composition, (c) a solvent comprising propylene glycol or a mixture of propylene glycol and ethanol in an amount of from about 15% to about 25% by weight of the total composition, and (d) a surfactant comprising Polysorbate 80 in an amount of from about 30% to about 45% by weight of the total composition .

Another preferred composition of the present invention comprises:

(a) a pyranone compound of formulas I, II, III or IV in an amount of from about 20% to about 30% by weight of the total composition, (b) a dimethylaminoethanol or tris(hydroxymethyl) aminomethane in an amount of from about 0.1% to about 7% by weight of the total composition, (c) a solvent comprising propylene glycol or a mixture of propylene glycol and ethanol in an amount of from about 15% to about 25% by weight of the total composition, (d) a surfactant comprising Cremophor RH40 or Cremophor EL in an amount of from about 30% to about 45% by weight of the total composition, and (e) one or more oils selected from the group consisting of monoolein, diolein, Campul MCM or Maisine in an amount of from about 5% to about 25% by weight of the total composition.

Optionally, the preferred compositions further comprise one or more oils in an amount of about 5% to about 25% by weight of the total composition.

In the preferred compositions of the present invention, the mixture of propylene glycol and ethanol is in a ratio of about 1:1.

In the preferred compositions of the present invention, an even more preferred composition comprises an dimethylaminoethanol or tris(hydroxymethyl)aminomethane in an amount of from about 0.1% to 5% by weight of the total composition.

In particular, the most preferred composition of the present invention comprises the pyranone compound of formula I.

The composition of the present invention may take the form of liquid for soft elastic capsules or hard gelatin capsules by oral application. The composition may also be in the form of liquid solution for oral, parenteral, rectal or topical application. The preferred dosage form is in the form of liquid for soft elastic capsules.

If desired, the compositions of the present invention may further comprise conventional pharmaceutical additives such as co-surfactant (for example, sodium lauryl sulfate), coloring agents, flavoring agents, fragrances, preserving agents, stabilizers, anti-oxidant and/or thickening agents.

The compositions of the present invention may be prepared in a conventional manner, for example, by dissolving an active agent in the solvent, then adding the amine, the surfactant and optionally an oil. The resulting solution is then formulated into the desired dosage form such as, for example, soft elastic capsules or hard gelatin capsules by known manufacturing technology.

The pharmaceutical compositions of the present invention will be better understood in connection with the following examples, which are intended as an illustration of and not a limitation upon the scope of the invention. Without further elaboration, it is believed that one skilled in the art can, using the preceding description and the information provided in the examples below, practice the present invention to its fullest extent.

A. General Procedure for Preparing the Compositions of the Present Invention Drug is placed in a container. A solvent comprising propylene glycol or a mixture of solvents selected from ethanol (95%) and propylene glycol (1:1 by weight) is added and the cap is tightened. The container is put in a water bath at about 60° C. and shaken gently until all of the drug material is dissolved. After the container is cooled down to room temperature, appropriate amounts of a basic amine, a surfactant and optionally one or more oils are added into the container. The container is sealed and put in a water bath at about 60° C. and shaken gently until a clear solution is formed. The container is usually left at ambient conditions for future use.

EXAMPLE 1

| Component | Weight (mg) | %, w/w |
| --- | --- | --- |
| The compound of formula I | 299 | 29.8 |
| EtOH/Propylene Glycol (1:1) | 250 | 25.0 |
| Polysorbate 80 | 375 | 37.5 |
| Ethanolamine | 60 | 6.0 |
| Sodium lauryl sulfate | 20 | 2.0 |

EXAMPLE 2

(The same formulation as the EXAMPLE 1 except without ethanolamine)

| Component | Weight (mg) | %, w/w |
| --- | --- | --- |
| The compound of formula I | 302 | 31.3 |
| EtOH/Propylene Glycol (1:1) | 258 | 26.8 |
| Polysorbate 80 | 385 | 39.9 |
| Sodium lauryl sulfate | 19 | 2.00 |

EXAMPLE 3

| Component | Weight (mg) | %, w/w |
| --- | --- | --- |
| The compound of formula I | 298 | 28.0 |
| EtOH/Propylene Glycol (1:1) | 200 | 18.6 |
| Cremophor EL | 505 | 47.5 |
| Dimethylaminoethanol | 63 | 5.8 |

EXAMPLE 4

| Component | Weight (mg) | %, w/w |
| --- | --- | --- |
| The compound of formula I | 296 | 29.6 |
| EtOH/Propylene Glycol (1:1) | 258 | 25.8 |
| Polysorbate 80 | 358 | 35.8 |
| Dimethylaminoethanol | 70 | 7.0 |
| Sodium lauryl sulfate | 18 | 1.8 |

EXAMPLE 5

| Component | Weight (mg) | %, w/w |
| --- | --- | --- |
| The compound of formula I | 303 | 29.5 |
| EtOH/Propylene Glycol (1:1) | 200 | 19.4 |
| Campul MCM | 65 | 6.3 |
| Cremophor EL | 450 | 43.3 |
| Diethanolamine | 15 | 1.4 |

EXAMPLE 6

| Component | Weight (mg) | %, w/w |
| --- | --- | --- |
| The compound of formula I | 301 | 26.2 |
| EtOH/Propylene Glycol (1:1) | 203 | 17.7 |
| Monoolein | 252 | 22.0 |
| Cremophor RH40 | 312 | 27.2 |

-continued

| Component | Weight (mg) | %, w/w |
|---|---|---|
| Ethanolamine | 62 | 5.4 |
| Sodium lauryl sulfate | 16 | 1.4 |

EXAMPLE 7

| Component | Weight (mg) | %, w/w |
|---|---|---|
| The compound of formula I | 302 | 26.2 |
| EtOH/Propylene Glycol (1:1) | 203 | 17.6 |
| Diolein | 264 | 22.9 |
| Cremophor RH40 | 305 | 26.4 |
| Ethanolamine | 64 | 5.6 |
| Sodium lauryl sulfate | 15 | 1.3 |

EXAMPLE 8

| Component | Weight (mg) | %, w/w |
|---|---|---|
| The compound of formula I | 303 | 29.5 |
| EtOH/Propylene Glycol (1:1) | 200 | 19.4 |
| Campul MCM | 65 | 6.3 |
| Cremophor EL | 450 | 43.3 |
| Dimethylaminoethanol | 15 | 1.4 |

EXAMPLE 9

| Component | Weight (mg) | %, w/w |
|---|---|---|
| The compound of formula I | 303 | 29.5 |
| EtOH/Propylene Glycol (1:1) | 200 | 19.4 |
| Campul MCM | 65 | 6.3 |
| Cremophor EL | 450 | 43.3 |
| Choline hydroxide | 15 | 1.4 |

EXAMPLE 10

| Component | Weight (mg) | %, w/w |
|---|---|---|
| The compound of formula I | 400 | 39.90 |
| EtOH (95% pure) | 100 | 9.97 |
| Propylene Glycol | 40 | 3.99 |
| Propyl gallate | 2.5 | 2.49 |
| Cremophor EL | 360 | 35.91 |
| Diethanolamine | 80 | 7.98 |
| H$_2$O | 20 | 1.99 |

EXAMPLE 11

| Component | Weight (mg) | %, w/w |
|---|---|---|
| The compound of formula I | 500 | 49.87 |
| EtOH (95%) | 90 | 8.98 |
| Propyl gallate | 2.5 | 0.25 |

-continued

| Component | Weight (mg) | %, w/w |
|---|---|---|
| Cremophor EL | 320 | 31.92 |
| Ethanolamine | 90 | 8.98 |

B. Oral Bioavailability Test (i) Oral Bioavailability Test in Rats

Sprague-Dawley male rats were selected for the in vivo oral bioavailability study. Each rat was prepared by the surgical implantation of an indwelling cannula in the superior vena cava. Each rat, in the weight range of 300–400 g, was fasted overnight prior to dosing. Each formulation was orally administered to a group of rats (n=3) at a 20 mg/kg dose. The formulations with high concentration of the compound of formula I (typically 200–300 mg/g) was diluted by 100-fold with water and injected directly into the rat's stomach using oral gavage. Serial blood samples of 0.25 ml were obtained from the indwelling cannula at 0.25, 0.5, 1, 2, 4, 6, 8, 12, and 24 hours after dosing. These blood samples were analyzed using a HPLC assay specific for the compound of formula I. Drug concentrations in the blood of the test rats are plotted against the time after the drug is administered through an intravenous (i.v.) or oral route and the AUCs (the Area Under the plasma concentration-time Curve) are integrated using the trapezoidal rule to calculate the absolute bioavailability.

$$\text{Absolute bioavailability}(F) = \frac{(AUC)_{oral}/Dose_{oral}}{(AUC)_{iv}/Dose_{iv}}$$

The present invention achieves the desired results as demonstrated in the absolute bioavailability test in Table 1. Comparing the reference example 2 (without basic amine) with the examples 1, 5, 6 and 7, the formulations of the present invention exhibit at least three times fold higher oral bioavailability.

TABLE 1

Oral Bioavailability Test in Rats

| Example No. | Absolute Mean Oral Bioavailability (%) |
|---|---|
| 1 | 65 |
| 2 | 17 |
| 5 | 96 |
| 6 | 66 |
| 7 | 58 |
| Aqueous suspension of free acid of the compound of formula I | <20 |

What is claimed is:
1. A pharmaceutical composition comprising:
(a) a pyranone compound of formula II as a pharmaceutically active agent,

II (b) an amine in an amount of from about 0.1% to about 10% by weight of the total composition,
(c) one or more pharmaceutically acceptable solvents, and
(d) one or more pharmaceutically acceptable surfactants;
wherein said solvent is propylene glycol, polypropylene glycol, polyethylene glycol, glycerol, ethanol, triacetin, dimethyl isosorbide, glycofurol, propylene carbonate, dimethyl acetamide or a mixture thereof;
wherein said surfactant is Polyoxyl 40 hydrogenated castor oil, Polyoxyl 35 castor oil, Polysorbate 20, Polysorbate 40, Polysorbate 60, Polysorbate 80, polyethylene glycol 12-hydroxy stearate, polyoxyethylene glyceryl trioleate, Polyoxyethylene stearates, Saturated Polyglycolyzed Glycerides, or Poloxamers;
wherein $R_1$ is H—;
$R_2$ is $C_3$-$C_5$ alkyl, phenyl-$(CH_2)_2$—, het-$SO_2NH$—$(CH_2)_2$—, cyclopropyl-$(CH_2)_2$-, F-phenyl-$(CH_2)_2$-, het-$SO_2NH$-phenyl-, or $F_3C$-$(CH_2)_2$—; or
$R_1$ and $R_2$ taken together are a double bond;
$R_3$ is $R_4$—$(CH_2)_n$—$CH(R_5)$—, $H_3C$—$[O(CH_2)_2]_2$—$CH_2$—, $C_3$-$C_5$ alkyl, phenyl-$(CH_2)_2$—, het-$SO_2NH$—$(CH_2)_2$—, $(HOCH_2)_3C$—NH—$C(O)$NH—$(CH_2)_3$—, $(HO_2C)(H_2N)CH$—$(CH_2)_2$—$C(O)$—NH—$(CH_2)_3$—, piperazin-1-yl-$C(O)$—NH—$(CH_2)_3$, $HO_3S(CH_2)_2$—$N(CH_3)$—$C(O)$—$(CH_2)_6$—$C(O)$—NH—$(CH_2)_3$—, cyclopropyl-$(CH_2)_2$—, F-phenyl-$(CH_2)_2$—, het-$SO_2NH$-phenyl, or $F_3C$—$(CH_2)_2$—;
n is 0, 1 or 2;
$R_4$ is phenyl, het, cyclopropyl, $H_3C$—$[O(CH_2)_2]_2$—, het-$SO_2NH$—, Br—, $N_3$—, or $HO_3S(CH_2)_2$—N$(CH_3)$—$C(O)$—$(CH_2)_6$—$C(O)$—NH—;
$R_5$ is —$CH_2$—$CH_3$, or —$CH_2$-cyclopropyl;
$R_6$ is cyclopropyl, $CH_3$—$CH_2$—, or t-butyl;
$R_7$ is —$NR_8SO_2$-het, —$NR_8SO_2$-phenyl, optionally substituted with $R_9$, —$CH_2$—$SO_2$-phenyl, optionally substituted with $R_9$, or —$CH_2$—$SO_2$-het;
$R_8$ is —H, or —$CH_3$;
$R_9$ is —CN, —F, —OH, or —$NO_2$;
wherein het is a 5-, 6- or 7-membered saturated or unsaturated ring containing from one to three heteroatoms selected from the group consisting of nitrogen, oxygen and sulfur; and including any bicyclic group in which any of the above heterocyclic rings is fused to a benzene ring or another heterocycle, optionally substituted with —$CH_3$, —CN, —OH, —$C(O)OC_2H_5$, —$CF_3$, —$NH_2$, or —$C(O)$—$NH_2$; or
a pharmaceutically acceptable salt thereof.
2. The pharmaceutical composition of claim 1 wherein the pyranone compound of formula II is a compound of formula

I.

I

3. A pharmaceutical composition comprising:
(a) a pyranone compound of formula III or IV as a pharmaceutically active agent,

III

IV (b) an armine in an amount of from about 0.1% to about 10% by weight of the total composition,
(c) one or more pharmaceutically acceptable solvents, and
(d) one or more pharmaceutically acceptable surfactants;
wherein said solvent is propylene glycol, polypropylene glycol, polyethylene glycol, glycerol, ethanol, triacetin, dimethyl isosorbide, glycofurol, propylene carbonate, dimethyl acetamide or a mixture thereof;
wherein said surfactant is Polyoxyl 40 hydrogenated castor oil, Polyoxyl 35 castor oil, Polysorbate 20, Polysorbate 40, Polysorbate 60, Polysorbate 80, polyethylene glycol 12-hydroxy stearate, polyoxyethylene glyceryl trioleate, Polyoxyethylene stearates, Saturated Polyglycolyzed
Glycerides, or Poloxamers;
wherein $R_{10}$ is H—, $CH_3O$—, or $CH_3O$—$[(CH_2)_2O]_3$—;
$R_{11}$ is cyclopropyl, or —$CH_2$—$CH(CH_3)_2$;
$R_{12}$ is —$NR_{14}SO_2$-phenyl, optionally substituted with $R_{15}$, —$NR_{14}SO_2$-het, —$CH_2$—$SO_2$-phenyl, optionally substituted with $R_{15}$, or —$CH_2$—$SO_2$-het;
$R_{13}$ is —H, —$(CH_2)_2$—$CH_3$, —$CH_2$-cyclopropyl, or —$CH_2$-phenyl;
$R_{14}$ is —H, or —$CH_3$; $R_{15}$ is —CN, —F, —$CH_3$, —COOH, or —OH; het is a 5-, 6- or 7-membered saturated or unsaturated ring containing from one to three heteroatoms selected from the group consisting of nitrogen, oxygen and sulfur; and including any bicyclic group in which any of the above heterocyclic rings is fused to a benzene ring or another heterocycle; optionally substituted with one or two —CH$_3$, —CN, —C(O)OC$_2$H$_5$, or —OH; or a pharmaceutically acceptable salt thereof.

4. The pharmaceutical composition of claim 1 or 3 wherein a compound of formula II, III or IV is in an amount of from about 1% to about 50%.

5. The pharmaceutical composition of claim 2 wherein a compound of formula I is in an amount of from about 20% to about 30%.

6. The pharmaceutical composition of claim 1 or 3 wherein the amine is lower alkylamine, basic amino acid, or choline hydroxide.

7. The pharmaceutical composition of claim 6 wherein the lower alkylamine is ethanolamine, diethanolamine, triethanolamine, tris(hydroxymethyl)aminomethane, ethylenediamine, or dimethylaminoethanol.

8. The pharmaceutical composition of claim 6 wherein the lower alkylamine is dimethylaminoethanol or tris(hydroxymethyl)aminomethane.

9. The pharmaceutical composition of claim 6 wherein the basic amino acid is arginine, lysine or guanidine.

10. The pharmaceutical composition of claim 1 or 3 wherein the amine is in an amount of from about 0.1% to about 7% by weight of the total composition.

11. The pharmaceutical composition of claim 1 or 3 wherein the amine is in am amount of from about 0.1% to about 5% by weight of the total composition.

12. The pharmaceutical composition of claim 1 or 3 wherein the pharmaceutically acceptable solvent is propylene glycol.

13. The pharmaceutical composition of claim 1 or 3 wherein the pharmaceutically acceptable solvent is a mixture solution comprising propylene glycol and 95% (v/v) ethanol in a ratio of about 1:1.

14. The pharmaceutical composition of claim 1 or 3 wherein the pharmaceutically acceptable solvent is in an amount of from about 10% to about 30% by weight of the total composition.

15. The pharmaceutical composition of claim 1 or 3 wherein the pharmaceutically acceptable solvent is in an amount of from about 15% to about 25% by weight of the total composition.

16. The pharmaceutical composition of claim 1 or 3 wherein the pharmaceutically acceptable surfactant is Polyoxyl 40 hydrogenated castor oil, Polyoxyl 35 castor oil, or Polysorbate 80.

17. The pharmaceutical composition of claim 1 or 3 wherein the pharmaceutically acceptable surfactant is Polyoxyl 40 hydrogenated castor oil.

18. The pharmaceutical composition of claim 1 or 3 wherein the pharmaceutically acceptable surfactant is Polyoxyl 35 hydrogenated castor oil.

19. The pharmaceutical composition of claim 1 or 3 wherein the surfactant is in an amount of from about 10% to about 50% by weight of the total composition.

20. The pharmaceutical composition of claim 1 or 3 wherein the surfactant is in an amount of from about 30% to about 45% by weight of the total composition.

21. The pharmaceutical composition of claim 1 or 3 wherein the composition further comprises one or more oils.

22. The pharmaceutical composition of claim 21 wherein said oil is soybean oil, avocado oil, squalene oil, sesame oil, olive oil, canola oil, corn oil, rapeseed oil, safflower oil, sunflower oil, fish oils, flavored oils, or a mixture thereof.

23. The pharmaceutical composition of claim 21 wherein said oil is monoolein, diolein, triolein, monolinoleate, dilinoleate, or trilinoleate.

24. The pharmaceutical composition of claim 21 wherein said oil is monoolein, diolein, monolinoleate, or dilinoleate.

25. The pharmaceutical composition of claim 21 wherein said oil is in an amount from about 5% to about 35% by weight of the total composition.

26. A pharmaceutical composition comprising:
    (a) a pyranone compound of formulas I as when in claim 1 in an amount of from about 20% to about 30% by weight of the total composition,
    (b) a dimethylaminoethanol or tnis(hydroxymethyl) aminomethane in an amount of from about 0.1% to about 5% by weight of the total composition,
    (c) a solvent comprising propylene glycol or a mixture of propylene glycol and 95% (v/v) ethanol in an amount of from about 15% to about 25% by weight of the total composition, and
    (d) a surfactant comprising Polysorbate 80 in an amount of from about 30% to about 45% by weight of the total composition.

27. The pharmaceutical composition of claim 26 wherein the mixture solution of propylene glycol and ethanol is in a ratio of about 1:1.

28. The pharmaceutical composition of claim 1, 3 or 26 which is a self-emulsifying formulation capable of generating emulsions or microemulsions upon mixing with sufficient aqueous media.

29. The pharmaceutical composition of claim 1, 3, or 26 which is in a form of liquid for soft elastic capsules.

* * * * *